US005620955A

United States Patent [19]
Knight et al.

[11] Patent Number: 5,620,955
[45] Date of Patent: Apr. 15, 1997

[54] BOMBESIN RECEPTOR ANTAGONISTS AND USES THEREOF

[75] Inventors: Martha Knight, Washington, D.C.; Kazuyuki Takahashi, Germantown; Bhaskar Chandrasekhar, Potomac, both of Md.

[73] Assignee: Peptide Technologies Corporation, Gaithersburg, Md.

[21] Appl. No.: 168,390

[22] Filed: Dec. 17, 1993

Related U.S. Application Data

[63] Continuation-in-part of Ser. No. 78,062, Jun. 18, 1993, abandoned.
[51] Int. Cl.$^6$ .............................. A61K 38/00; C07K 7/08
[52] U.S. Cl. .............................. 514/14; 514/15; 530/326; 530/327
[58] Field of Search .................................. 530/326, 327; 514/14, 15

[56] References Cited

U.S. PATENT DOCUMENTS

| | | | |
|---|---|---|---|
| 4,943,561 | 7/1990 | Heimbrook et al. | 514/17 |
| 5,019,647 | 5/1991 | Riemen et al. | 530/329 |
| 5,169,862 | 12/1992 | Burke et al. | 514/450 |
| 5,217,955 | 6/1993 | Bogden et al. | 514/12 |
| 5,244,883 | 9/1993 | Cai et al. | 514/15 |

FOREIGN PATENT DOCUMENTS

WO92/02545  2/1992  WIPO.

OTHER PUBLICATIONS

Halpern, "New Conc. Allergy Clin. Immunol.", Proc. Int. Congr. Allergol., 7th, (1971). Abstract.
Knight et al. "Society for Neuroscience", Abstracts, vol. 19, Part 2. (1993), p. 1270. Ab #525.7.
Bertaccini et al., "Gastrin Release By Bombesin in the Dog", Br. J. Pharmacol. 52:219–225 (1974).
Brambilla et al., "Heterotransplantation of Small Cell Lung Carcinoma into Nude Mice", Cancer 64:1238–1247 (Sep. 15, 1989).
Camble et al., "N–Isobutyryl–His–Trp–Ala–Val–D–Ala–His–Leu–NHMe (ICI 216140) A Potent in vivo antagonist analogue of bombesin/gastrin releasing peptide (Bn/GRP) derived from the C–terminal sequence lacking the final methionine residue", Life Sci. 45:1521–1527 (1989).
Camble et al., "ICI 216140 and other potent in vivo antagonist analogs of bombesin/gastrin–releasing peptide", Peptides: Chemistry, Structure & Biology, Riviers et al., eds., ESCOM, Leiden pp. 174–176 (1990).
deCastiglione et al., "Irreversible ligands for bombesin receptors", Peptides: Chemistry, Structure & Biology, Riviers et al. eds., ESCOM, Leiden pp. 168–170 (1990).
Coy et al., "Progress in the Development of Competitive Bombesin Antagonists", Ann. N.Y. Acad. Sci. 547:150–157 (1988).
Coy et al., "Probing Peptide Backbone Function in Bombesin", J. Biol. Chem. 263:5056–5060 (Apr. 15, 1988).
Coy et al., "Short–Chain Pseudopeptide Bombesin Receptor Antagonists with Enhanced Binding Affinities for Pancreatic Acinar and Swiss 3T3 Cells Display Strong Antimitotic Activity", J. Biol. Chem. 264:14691–14697 (Sep. 5, 1989).
Coy et al., "Short Chain Bombesin Pseudopeptides with Potent Bombesin Receptor Antagonist Activity in Rat and Guinea Pig Pancreatic Acinar Cells", European J. Pharmacol. 190:31–38 (1990).
Crawley, J., "Comparative Distribution of Cholecystokinin and Other Neuropeptides", Ann. N.Y. Acad. Sci. 448:1–8 (Jul. 5, 1985).
Cuttitta et al., "Bombesin–like peptides can function as autocrine growth factors in human small–cell lung cancer", Nature 316:823–826 (Aug. 29, 1985).
Erspamer et al., "Nomenclature Meeting: Report and Recommendations", Bombesin–Like Peptides in Health and Disease: Annals N.Y. Acad. Sci. 547:1–2 (1988).
Erspamer, V., "Discovery, Isolation, and Characterization of Bombesin–like Peptides", Bombesin–Like Peptides in Health and Disease: Annals N.Y. Acad. Sci. 547:3–9 (1988).
Gibbs et al., "Bombesin suppresses feeding in rats", Nature 282:208–210 (Nov. 8, 1979).
Heimbrook et al., "Carboxyl–terminal Modification of a Gastrin Releasing Peptide Derivatives Generates Potent Antagonists", J. Biol. Chem. 264:11258–11262 (Jul. 5, 1989).
Howard et al., "Bombesin–induced residual stimulation of amylase release from mouse pancreatic acini", Am. J. Physiol. 248:G196–199 (1985).
Kim et al., "C–terminal modified bombesin and litorin analogs with potent in vitro and in vivo antiproliferative activity", Peptides: Chemistry, Structure & Biology, Riviers et al., eds., ESCOM, Leiden, pp. 182–184 (1990).

(List continued on next page.)

Primary Examiner—Christina Y. Chan
Assistant Examiner—S. G. Marshall
Attorney, Agent, or Firm—Sterne, Kessler, Goldstein & Fox P.L.L.C.

[57] ABSTRACT

Bombesin is an amphibian peptide that has a structure closely related to that of several mammalian peptides, including Gastrin Releasing Peptide (GRP) and Neuromedins B and C. Bombesin, GRP and related peptides exert their in vivo effects by binding to specific receptors present on cells of the gastrointestinal tract, the central nervous system, and tumors. The invention relates to novel bombesin derivatives which act as bombesin receptor antagonists by blocking the binding of bombesin, GRP or related peptides to cellular receptors. By blocking the binding of bombesin, GRP and related peptides to cellular receptors on cancer cells, these antagonists inhibit the growth of tumor cells that respond to the growth-promoting action of bombesin. These antagonists are expected to block the binding of bombesin, GRP or related peptides to similar receptors on cells in the gastrointestinal tract or the central nervous system. Thus, these antagonists have therapeutic use in the treatment or prevention of conditions mediated by bombesin, GRP or related peptides, including cancer and gastrointestinal disorders such as peptic ulcer, pancreatitis, and feeding disorders.

17 Claims, 2 Drawing Sheets

OTHER PUBLICATIONS

Knight et al., "Design of a cyclic bombesin analog", *Peptides: Chemistry, Structure & Biology*, Riviers et al., eds., ESCOM, Leiden, pp. 185–187 (1990).

Knight et al., "Bombesin Antagonists: Synthesis and Inhibitory Action on Small Cell Lung Carcinoma (SCLC) Tumor Growth and Pancreatic Acinar Cell Function", *Thirteenth American Peptide Symposium; Peptide Inhibitors*:P523 (Jun. 1993).

Knight et al., "Biological Activity of a Potent Bombesin Receptor Antagonist", *Soc. Neurosci. Abst.* 19(II):525.7 (Nov. 1993).

Leban et al., "Development of potent gastrin–releasin peptide antagonist having a D–Pro–ψ($CH_2NH$)–Phe–$NH_2$ C terminus", *Proc. Natl. Acad. Sci. USA* 90:1922–1926 (Mar. 1993).

Leban et al., "Structure–Activity Relationship Study of Gastrin–Releasing Peptide Antagonists Having a C–Terminal DPROψ($CH_2NH$)PHE–$NH_2$", *Thirteenth American Peptide Symposium; Biologically Active Peptides*:P344 (Jun. 1993).

Mahmoud et al., "Small Cell Lung Cancer Bombesin Receptors are Antagonized by Reduced Peptide Bond Analogues", *Life Sci.* 44:367–373 (1989).

Mahmoud et al., "[$Psi^{13,14}$] Bombesin Analogues Inhibit Growth of Small Cell Lung Cancer in Vitro and in Vivo", *Cancer Res.* 51:1798–1802 (Apr. 1, 1991).

Marki et al., "Bombesin Analogs: Effects on Thermoregulation and Glucose Metabolism", *Peptides* 2:169–177 (1981).

McDonald et al., "Characterization of a Gastrin Releasing Peptide from Porcine non–antral Gastric Tissue", *Biochem. & Biophys. Res. Comm.* 90:227–233 (Sep. 12, 1979).

Minamino et al., "Neuromedin B: A Novel Bombesin–Like Peptide Identified in Porcine Spinal Cord", *Biochem. & Biophys. Res. Comm.* 114:541–548 (Jul. 29, 1983).

Minamino et al., "Neuromedin C: A Bombesin–Like Peptide Identified in Porcine Spinal Cord", *Biochem. & Biophys. Res. Comm.* 119:14–20 (Feb. 29, 1984).

Mokotoff et al., "Novel GRP analogs which are potent antagonists of bombesin–like peptides", *Peptides: Chemistry, Structure & Biology*, Riviers et al., eds., ESCOM, Leiden pp. 63–65 (1990).

Moody et al., "Bombesin: Specific binding to rat brain membranes", *Proc. Natl. Acad. Sci. USA* 75:5372–5376 (Nov. 1978).

Moody et al., "Bombesin–like Peptides in Rat Brain: Quantitation and Biochemical Characterization", *Biochem. & Biophys. Res. Comm.* 90:7–14 (Sep. 12, 1979).

Moody et al., "High Affinity Receptors for Bombesin/GRP–Like Peptides on Human Small Cell Lung Cancer", *Life Sci.* 37:105–113 (1985).

Moody et al., "BW–2258: A New Gastrin Releasing Peptide Receptor Antagonist", *Soc. Neurosc. Abst.* 19(II):525.10 (Nov. 1993).

Mukai et al., "Antagonism by GRP(18–27) and Substance P Analogues on Insulin Release Stimulated by GRP(18–27)", *Peptides* 11:173–175 (1990).

Mulshine et al., "Clinical Use of a Monoclonal Antibody to Bombesin–like Peptide in Patients with Lung Cancer", *Annal. N.Y. Acad. Sci.* 547:360–372 (1988).

Nakajima et al., "Immunohistochemical Study of Small Cell Lung Carcinoma; With Special Reference to the Neuroendocrine Markers Aromatic L–Amino Acid Decarboxylase and Gastrin–Releasing Peptide", *Jpn. J. Clin. Oncol.* 16:223–233 (Sep. 1986).

Porrecca et al., "Central and Peripheral Visceral Effects of Bombesin", *Annal. N.Y. Acad. Sci.* 547:194–203 (1988).

Pullan et al., "Ectopic production of methionine enkephalin and beta–endorphin", *Br. Med. J.* 1:758–759 (Mar. 15, 1980).

Rivier et al., "Bombesin, Bombesin Analogues, and Related Peptides: Effects on Thermoregulation", *Biochem.* 17:1766–1771 (1978).

Rozengurt, E., "Early Signals in the Mitogenic Response", *Science* 234:161–166 (Oct. 10, 1986).

Saeed et al., "Effect of Substitutions in Position 12 of Bombesin on Antagonist Activity", *Peptides* 10:597–603 (1989).

Sigma Catalogue: Peptides and Amino Acids, p. 30, (1993–1994).

Spindel & Krane, "Molecular Biology & Bombesin–Like Peptides", *Bombesin–Like Peptides in Health and Disease:Annals N.Y. Acad. Sci.* 547:10–20 (1988).

Sporn & Roberts, "Autocrine growth factors and cancer", *Nature* 313:745–747 (Feb. 28, 1985).

Staley et al., "[Des–$Met^{14}$]Bombesin Analogues Function as Small Cell Lung Cancer Bombesin Receptor Antagonists", *Peptides* 12:145–149 (1991).

Thomas et al., "Antitumoral Activity of Bombesin Analogues on Small Cell Lung Cancer Xenografts: Relationship with Bombesin Receptor Expression", *Cancer Research* 52:4872–4877 (Sep. 15, 1992).

Trepel et al., "A Novel Bombesin Receptor Antagonist Inhibits Autocrine Signals in a Small Cell Lung Carcinoma Cell Line", *Biochem. & Biophys. Res. Comm.* 156:1383–1389 (Nov. 15, 1988).

Wang et al., "Des–Met Carboxyl–terminally Modified Analogues of Bombesin Function as Potent Bombesin Receptor Antagonists, Partial Agonists, or Agonists", *J. Biol. Chem.* 265:15695–15703 (Sep. 15, 1990).

Zachary & Rozengurt, "High–Affinity receptors for peptides of the bombesin family in Swiss 3T3 cells", *Proc. Natl. Acad. Sci. USA* 82:7616–7620 (Nov. 1985).

Bombesin (SEQ ID No.:1)

```
        1    2    3    4   5    6    7    8    9   10  11   12  13   14
       pGlu-Gln-Arg-Leu-Gly-Asn-Gln-Trp-Ala-Val-Gly-His-Leu-Met-NH2
```

Cyclic Analogs of Bombesin

| Compound Name | Structure |
|---|---|
| PTC 803. | H₃C-C(=O)-Lys-Asn-Gln-Trp-Ala-Val-Ala-His-Leu, cyclized via NHCO |
| PTC 804. | H₃C-C(=O)-D-Lys-Asn-Gln-Trp-Ala-Val-D-Ala-His-Leu, cyclized via NHCO |
| PTC 805. | H₃C-C(=O)-D-Lys-Asn-Gln-Trp-Ala-Val-Ala-His-Leu, cyclized via NHCO |
| PTC 806. | H₃C-C(=O)-Lys-Asn-Gln-Trp-Ala-Val-D-Ala-His-Leu, cyclized via NHCO |
| PTC 807. | (Phenyl)-D-Lys-Asn-Gln-Trp-Ala-Val-D-Ala-His-Leu, cyclized via NHCO |
| PTC 808. | Naphthoyl-D-Lys-Asn-Gln-Trp-Ala-Val-D-Ala-His-Leu, cyclized via NHCO |
| PTC 809. | N-(2,4-dinitrophenyl)-D-Lys-Asn-Gln-Trp-Ala-Val-D-Ala-His-Leu, cyclized via NHCO |
| PTC 811. | H₃C-C(=O)-Lys-Trp-Ala-Val-D-Ala-His-Leu, cyclized via NHCO |
| PTC 812. | H₃C-C(=O)-Lys-Trp-Ala-Val-D-Ala-His-D-Glu-propylamide, cyclized via NHCO |

Linear Analogs of Bombesin

Bombesin (SEQ ID No.:1)

```
           1    2   3   4   5   6   7   8   9  10  11  12  13  14
         pGlu-Gln-Arg-Leu-Gly-Asn-Gln-Trp-Ala-Val-Gly-His-Leu-Met-NH2
```

| Compound Name | Structure |
|---|---|
| PTC 815. | Cl-CH₂CH₂, N-C₆H₄-CH₂CH₂CH₂CH₂-C(=O)-Asn-Gln-Trp-Ala-Val-D-Ala-His-Leu-C(=O)-OCH₂CH₃ with Cl-CH₂CH₂ |
| PTC 815B. | Cl-CH₂CH₂, N-C₆H₄-CH₂CH₂CH₂CH₂-C(=O)-Asn-Gln-Trp-Ala-Val-D-Ala-His-Leu-C(=O)-OCH₂CH₃ with OH-CH₂CH₂ |
| PTC 816. | Br-CH₂-C(=O)-Asn-Gln-Trp-Ala-Val-D-Ala-His-Leu-C(=O)-OCH₂CH₃ |
| PTC 818. | H₃C-C(=O)-His-Trp-Ala-Val-D-Ala-His-Leu-C(=O)-OCH₂CH₃ |
| PTC 820. | H₃C-C(=O)-His-Trp-Ala-Val-D-Ala-His-NHCH₂CH₂-C₆H₄-Br |
| PTC 821. | Cl-CH₂CH₂, N-C₆H₄-CH₂CH₂CH₂CH₂-C(=O)-His-Trp-Ala-Val-D-Ala-His-Leu-C(=O)-OCH₂CH₃ with Cl-CH₂CH₂ |

BOMBESIN RECEPTOR ANTAGONISTS AND USES THEREOF

STATEMENT AS TO RIGHTS TO INVENTIONS MADE UNDER FEDERALLY-SPONSORED RESEARCH AND DEVELOPMENT

This invention was made with U.S. government support under SBIR Grant No. 1R43CA55468-01, awarded by the National Institutes of Health and the National Cancer Institute. The U.S. government has certain rights in the invention.

CROSS-REFERENCE TO RELATED APPLICATIONS

This application is a continuation-in-part of U.S. Ser. No. 08/078,062, filed Jun. 18, 1993 now abandoned, the contents of which are fully incorporated by reference herein.

BACKGROUND OF THE INVENTION

1. Field of the Invention

The neuropeptide bombesin exerts physiological effects by binding to specific receptors present on cells in the gastrointestinal tract and central nervous systems. Bombesin also binds to, and promotes the growth of, some types of tumor cells. The invention relates to novel bombesin derivatives which act as antagonists of bombesin, or related peptides such as gastrin releasing peptide, by blocking the binding of such peptides to their cognate receptors. By blocking the binding of bombesin-like peptides to their receptors, these antagonists block the physiological effects of these peptides and inhibit the growth of tumor cells that respond to the growth-promoting action of bombesin. Thus, these antagonists have therapeutic use in the treatment or prevention of some types of cancer, in controlling physiological effects in gastrointestinal disorders such as peptic ulcers or pancreatitis, and in modulating responses of the central nervous system including those that occur in feeding disorders or hypothermia.

2. Brief Description of the Background Art

Bombesin (hereinafter referred to as BBN) was discovered in 1970 as a potent smooth muscle contracting agent of nonmammalian origin first isolated from amphibian skin (Erspamer et al., *J. Pharm. Pharmacol.* 22:275 (1970)). Immunolocalization has indicated the presence of both BBN-like peptides and BBN receptors in the mammalian central nervous system and gastrointestinal tract. (Moody et al., *Proc. Natl. Acad. Sci. USA* 75:5372 (1978)). BBN-like peptides function in feeding and satiety and stimulate gastrin release and pancreatic exocrine secretion (Gibbs et al., *Nature* 282:208 (1979)); Bertaccini et al.,*Br. J. Pharmac.* 59:219 (1974)). As determined by immunolocalization, BBN-like peptides are present in moderate amounts in discrete areas of the brain such as the lateral hypothalamus, which controls feeding behavior and body temperature (Crawley, J., *Ann. N.Y. Acad. Sci.* 448:1 (1985)). BBN also potently produces hypothermia in cold-adapted rats upon central nervous systems (CNS) and peripheral administration. The first significant structure-activity studies of BBN conducted with synthesized analogs measured hypothermia and brain receptor binding as indicators of CNS activity. (Rivier and Brown, *Biochem.* 17:1766 (1978); Marki et al., *Peptides* 2:169 (1981); Moody et al., *Proc. Natl. Acad. Sci. USA* 75:5372 (1978)).

The sequence of BBN has been determined and is (SEQ ID No.:1)

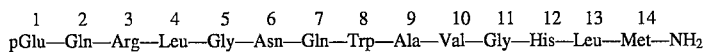

wherein pGlu indicates pyroglummic acid and Met-NH₂ indicates methionine amide. (Erspamer, V., *Ann. New York Acad. Sci.* 547:3 (1988)).

Mammalian proteins related to BBN are known and include gastrin releasing peptide (hereinafter referred to as GRP) and neuromedins B and C. GRP is a 27 residue peptide that has a sequence (i.e., Val-Pro-Leu-Pro-Ala-Gly-Gly-Gly-Thr-Val-Leu-Thr-Lys-Met-Tyr-Pro-Arg-Gly-Asn-His-Gly-Tep-Ala-Val-Gly-His-Leu-Met-NH₂; SEQ ID No.:15) that includes a carboxyl terminal sequence that is clearly related to the sequence of BBN (MacDonald et al., *Biochem Biophys. Res. Commun.* 90:227 (1979)). As predicted by the effects of BBN on mammalian central nervous system activities, such as the regulation of cardiovascular functions (Fisher et al., *Amer. J. Physiol.: Heart and Circulatory Physiol.* 17:H425 (1985)), and the immunoreactivity of antibodies to BBN and GRP to tissues of the brain and spinal cord (Panula et al., *Ann. New York Acad. Sci.* 547:54 (1988), BBN/GRP-like peptides are found in the CNS. Neuromedins B and C were originally isolated from the porcine CNS. Neuromedin B is a 32 residue peptide that has a sequence (Ala-Pro-Leu-Ser-Trp-Asp-Leu-Pro-Glu-Pro-Arg-Ser-Arg-Ala-Ser-Lys-Ile-Arg-Val-His-Ser-Arg-Gly-Asn-Leu-Trp-Ala-Thr-Gly-His-Phe-Met-NH₂; SEQ ID No.:16) that includes a carboxyl terminal sequence that is clearly related to the carboxyl termini of BBN and GRP, and neuromedin C is a decapeptide that is identical to the carboxyl-terminus of GRP (i.e., Gly-Asn-His-Trp-Ala-Val-Gly-His-Leu-Met-NH₂; SEQ ID No.:2) (Minamino et al., *Biophys. Res. Comm.* 114:541 (1983); Minamino et al., *Biochem. Biophys. Res. Comm.* 119:14 (1984)).

Although the term "bombesin receptors" is used and accepted in the art, bombesin per se does not exist in mammalian systems. That is, the in vivo role of bombesin receptors is not to bind BBN, an amphibian peptide; rather, when used in regard to mammalian systems, the term "bombesin receptors" refers to a class of cellular receptors that bind GRP, neuromedin B or C, or other BBN-related peptides endogenous to mammals. Because BBN is closely related to GRP and similar peptides, these receptors also bind BBN. The fact the BBN not only binds to receptors on mammalian cells, but also stimulates the same intracellular effects as GRP, further indicates the close relatedness of BBN to GRP. This high degree of relatedness indicates that changes in the peptide sequences of BBN or GRP that substitute an amino acid found in one peptide for the amino acid found in the corresponding position in the other peptide will not produce functional differences. Moreover, chemical modifications that have a desirable effect on one member of the BBN/GRP-like family of peptides are expected to be readily applicable to any other member.

Nomenclature of the BBN/GRP-like family of peptides is complicated by the fact that the peptides are synthesized in vivo with amino-terminal signal peptides and multiple forms of the GRP precursor, containing differing carboxyl-terminal extension peptides (CTEPs), are known to be expressed in various cell lines (Hamad et al., *Virchows Arch.* 411:185 ( 1987); MacDonald et al., *Biochem Biophys. Res. Commun.* 90:227 (1979)). Ultimately, a BBN/GRP precursor molecule is processed to release the amino-terminal signal peptide and the CTEP, and the BBN/GRP-like peptide itself. Interestingly, both mammalian and amphibian members of the BBN/GRP family share these complex regulatory features (Spindel et al., *Ann. New York Acad. Sci.* 547:10 (1988)). In any event, a system of nomenclature for the BBN/GRP-like family of peptides has been proposed (Erspamer et al., *Ann. New York Acad. Sci.* 547:1 (1988)) and is followed herein.

BBN is one of the most powerful growth factors capable of acting alone to stimulate the mitotic growth and proliferation of cells. (Rozengurt, E., *Science* 234:161 (1986)). Because BBN is a highly effective mitogen, inhibitors of BBN can prevent growth and proliferation of cells, as has been shown for Swiss 3T3 fibroblasts, small cell lung carcinoma (SCLC) and neuroblastoma cells. Early events in the induction of mitotic growth of Swiss 3T3 fibroblast cells, as well as other embryonic and cancer cells, have been characterized. Biochemical indicators of early events in the mitogenic response include increases in intracellular $Ca^{++}$ levels, protein kinase C activation, and thymidine uptake. The initial event in induction of mitogenic growth, binding of a BBN/GRP-like peptide to a cellular receptor, is also a biochemical event that can be monitored with appropriate assays.

The current state of the art shows a role for peptide receptors in carcinogenesis and tumor metastases. Receptors for GRP and the role of BBN/GRP-like peptides as autocrine growth factors for these cells have been described (Moody and Pert, *Biochem Biophys. Res. Commun.* 90:7 (1979)). High levels of BBN/GRP-like peptides and their receptors have been found in SCLC cells (Pullan et al., *Br. Med. J.* 1:758 (1980)). Cellular control through peptide receptors has also been demonstrated for breast and prostate gland tumors, and pancreatic carcinomas which can be treated with somatostatin analogues (Redding and Schally, *Proc. Natl. Acad. Sci. USA* 81:248 (1984); Redding and Schally, *Proc. Natl. Acad. Sci. USA* 78:6509 (1981); Hierowski et al., *F.E.B.S. Letters* 179:252 (1985)). In addition, malignant cells are known to be chemotactic for certain peptides. In particular, SCLC cells are known to have high-affinity receptors for BBN, GRP and related peptides (Moody et al., *Life Sci.* 37:105 (1985)).

Because of the role in cellular receptors in inducing the mitotic growth of cells, it was thought that substances that prevent the interaction of BBN/GRP-like peptides with their receptors might have an anti-mitotic effect upon BBN- and GRP-responsive tumor cell lines.

SCLC, which accounts for 20% of lung tumors, often includes cell lines that secrete GRP and demonstrate a mitogenic response when treated with BBN (Thomas et al., *Cancer Res.* 52:4872 (1992)). SCLC cell lines may be isolated from tumors and tested in vitro for their response to potential bomesin receptor antagonists (Trepel et al., *Biochem. Biophys. Res. Commun.* 156:1383 (1988); Mahmoud et al., *Life Sci.* 44:367 (1989)). Cultured SCLC cells, or biopsy samples containing SCLC cells, produce tumors when subcutaneously introduced into athymic nude mice (Brambilla et al., *Cancer (Phila.)* 64:1238 (1989)). The potency of antitumor agents may be examined in such mice, thus allowing potential anticancer agents to be evaluated in a live animal model (Cuttitta et al., *Nature* 316: 823 (1985)). Thus, SCLC is a useful system for developing antitumor agents to treat BBN/GRP-responsive cancers.

A monoclonal antibody that binds the carboxy-terminal portions of BBN and GRP, and which prevents the binding of GRP to its receptors, inhibits the in vitro and in vivo growth of SCLC cells (Cuttitta et al., *Nature* 316: 823 (1985)). The clinical use of this monoclonal antibody is being investigated (Mulshine et al., *Ann. New York Acad. Sci.* 547:360 (1988)).

Recently, attempts have been made to develop BBN/GRP antagonists that bind to cellular receptors by synthesizing chemical structures that are derived from the structures of BBN or GRP. Such receptor antagonists would inhibit the physiological effects stimulated by endogenous BBN/GRP-like peptides by limiting the ability of cells to bind these peptides.

Chemical structures derived from BBN include derivatives of BBN which retain 14 amino acid residues but in which dextrorotatory aromatic residues have been substituted for $His^{12}$ (Coy et al., *Ann. New York Acad. Sci.* 547:150 (1988); Saeed et al., *Peptides* 10:597 (1989)), derivatives of the carboxyl terminal 7–14 octapeptide in which Leu replaces $Met^{14}$ and individual peptide bonds are reduced (Coy et al., *J. Biol. Chem.* 263:5056 (1988); Coy et al., *J. Biol. Chem.* 264:14691 (1989)) or in which N-isobutyryl-His replaces $Gln^7$ and dextrorotatory Alanine replaces $Gly^{11}$ (Camble et al., *Life Sci.* 45:1521 (1989)), and derivatives of the carboxyl terminal 6–13 octapeptide in which D-Phe replaces $Phe^6$ and in which the absent $Met^{14}$ residue is replaced by a series of des-$Met^{14}$ alkylamides and esters (Staley et al., *Peptides* 12:145 (1991); Wang et al., *J. Biol. Chem.* 265:15695 (1990)). Other BBN analogs, as well as GRP analogs, have been described (Coy et al., *J. Biol. Chem.* 264:14691 (1989); Cai et al., U.S. Pat. No. 5,244,883; Kull et al., WO 92/02545; Heimbrook et al., *J. Biol. Chem.* 264:11258 (1989); Heimbrook et al., U.S. Pat. No. 4,943, 561; Riemen et al., U.S. Pat. No. 5,019,647; Mukai et al., *Peptides* 11:173 (1990); Leban et al., *Proc. Natl. Acad. Sci. USA* 90:1922 (1993)); See also Camble et al., Kim et al., Mokotoff et al. and Castiglione et al. in *Peptides: Chemistry, Structure and Biology*, Rivier and Marshall, eds., ESCOM, Leiden, p. 174, p. 182, p. 63 and p. 168, respectively (1990)).

Despite the fact that a number of derivatives of BBN have been prepared, a need still exists for effective bombesin receptor antagonists that possess adequate in vivo stability for therapeutic purposes. Compounds which act as BBN/GRP antagonists in one system may also act as partial agonists in other systems (Coy et al., *Eur. J. Phramacol.* 190:31 (1990)). Moreover, some BBN/GRP antagonists are reversible. For example, a reduced peptide bond antagonist ([$Psi^{13,14}$, $Leu^{14}$]BBN) inhibits growth with moderate potency (i.e., $K_i$=30 nM), but the effects of this antagonist are clearly reversed in a few minutes by the addition of BBN (Coy et at., *J. Biol. Chem.* 263:5056 (1988); Mahoud et al., *Cancer Res.* 51:1798 (1991)). Furthermore, some inhibitory analogues that have a potency in vitro that is similar to that of [$Psi^{13,14}$, $Leu^{14}$]BBN have been found, when tested, to be less potent than this antagonist in inhibiting SCLC growth in cultures and in vivo. This loss of potency may be due to susceptibility of the compound to proteolytic degradation. Some inhibitors are equipotent to GRP in binding assays and inhibit GRP-stimulated effects in human SCLC cells in vitro and in murine tissues in vivo, yet they do not actually inhibit the growth of SCLC cells in vitro (Heimbrook et al., *Peptides: Chemistry, Structure and Biology*, Rivier and Marshall, eds., ESCOM, Leiden, p. 185 (1990)). Therefore, a need exists for the development of other potent BBN antagonists that do not have agonist activity, that are resistant to proteolysis and not easily reversible, and are thus more effective for a longer period of time in vivo.

Peptide hormone receptor antagonists are a current approach to new anti-tumor chemotherapeutic drugs. Since tumors are derived from endocrine cell types, they have cell surface peptide receptors, secrete peptide hormones and display a growth response to peptides (Moody et al., Science 214:1246 (1981)). Certain peptides, such as BBN and GRP, function as autocrine growth factors for such tumors (Sporn and Roberts, Nature 313:745 (1985); Zachary and Rozengurt, Proc. Natl. Acad. Sci. USA 82:7616 (1985)). One example of a tumor cell line which exhibits growth in response to a peptide is human SCLC, which demonstrates a mitogenic response to GRP, the mammalian homologue of BBN ((Moody et al., Science 214:1246 (1981); Sporn and Roberts, Nature 313:745 (1985); Carney et al., Clin. Res. 31:404A (1983); Cuttitta et al., Nature 316:823 (1985)). It is now known that SCLC is a transformed neuroendocrine cell type which secretes, and has receptors for, GRP. Some recently reported bombesin receptor antagonists are known to inhibit growth of SCLC cells in vitro, yet do not demonstrate the same efficacy when administered in vivo (Mahoud et al., Cancer Res. 51 (1798–1802)). Therefore, a need also exists for the development of bombesin antagonists containing structural modifications which enhance stability and specificity for in vivo use.

SUMMARY OF THE INVENTION

The invention relates to the discovery of certain modified peptides which have potent BBN/GRP-like peptide antagonist activity. In particular, the invention relates to BBN receptor antagonists that are peptides, wherein the carboxy-terminal residue comprises an ethyl ester, having the following sequence (SEQ ID Nos.: 3–10):

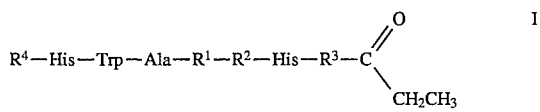

wherein $R^1$ is Val or Thr, $R^2$ is Gly or D-Ala, $R^3$ is Leu or Phe, and $R^4$, the amino terminal group, is Acetyl, Bromoacetyl, Chloroacetyl, [bis(2-chloroethyl)amino]-L-Phe, or

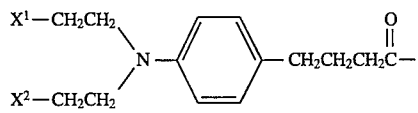

wherein $X^1$ is Cl or OH and $X^2$ is Cl or OH; and BBN receptor antagonists that are peptides, wherein the carboxy-terminal residue comprises an ethyl ester, having the sequence (SEQ ID Nos.:11–14):

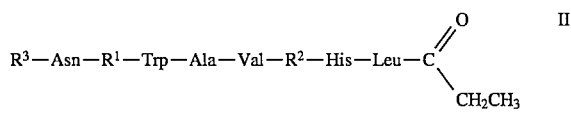

wherein $R^1$ is Gln or His, $R^2$ is Gly or D-Ala, and $R^3$, the amino terminal group, is Acetyl, Bromoacetyl, Chloroacetyl, [bis(2-chloroethyl)amino]-L-Phe, or

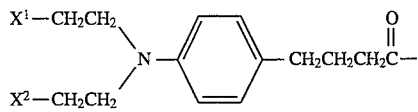

wherein $X^1$ is Cl or OH and $X^2$ is Cl or OH.

The invention further relates to a method of inhibiting the growth of cells that are sensitive to the growth-promoting activity of BBN/GRP-like peptides in a mammal, comprising administrating a therapeutically effective amount of the compounds in combination with a pharmaceutically acceptable carrier. The invention also relates to a method of inhibiting the binding of BBN/GRP-like peptides to cells capable of said binding, which comprises exposing the cells to an amount of the compound which is effective to inhibit binding.

BRIEF DESCRIPTION OF THE DRAWINGS

FIG. 1 shows the chemical structures of cyclic synthetic analogs of bombesin.

FIG. 2 shows the chemical structures of linear synthetic analogs of bombesin.

DETAILED DESCRIPTION OF THE PREFERRED EMBODIMENTS

In view of the numerous physiological effects of the BBN, GRP and other related peptides, and particularly their role as cell mitogens, the need for stable potent receptor antagonists of these peptides for therapeutic use is significant. The inventors have discovered bombesin antagonists consisting of a minimal portion of BBN (amino acid residues 6–13 or 7–13) in combination with two terminal inhibiting structures or polypeptide "caps" which serve to protect the compounds from in vivo proteolysis. The "caps" are positioned at the termini of the antagonists; specifically, an acetyl group or derivative thereof, or an alkylating agent, at the amino terminus, and an ethyl ester at the carboxyl terminus. The inventors have also discovered that peptides comprising the terminal inhibiting structures have highly potent BBN-antagonist effects that persist for extended periods of time in biological assays. The inventors have demonstrated the bombesin antagonist effects of these compounds for a variety of biological systems.

Therefore, in one embodiment (Formula I) the invention comprises peptides, wherein the carboxy-terminal residue comprises an ethyl ester, having the following sequence (SEQ ID Nos.:3–10):

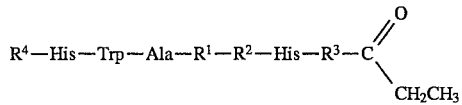

wherein $R^1$ is Val or Thr, $R^2$ is Gly or D-Ala, $R^3$ is Leu or Phe, and $R^4$, the amino terminal group, is Acetyl, Bromoacetyl, Chloroacetyl, or [bis(2-chloroethyl)amino]-L-Phe. Preferably, $R^4$ may be the chlorambucil group or a derivative thereof, i.e.,

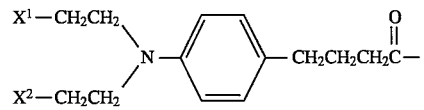

wherein $X^1$ is Cl or OH and $X^2$ is Cl or OH.

Preferable embodiments of the Formula I compounds include PTC 818, in which $R^1$ is Val, $R^2$ is D-Ala, $R^3$ is Leu and $R^4$ is an Acetyl group, and PTC 821 in which $R^1$ is Val, $R^2$ is D-Ala, $R^3$ is Leu and $R^4$ is chlorambucil, i.e.,

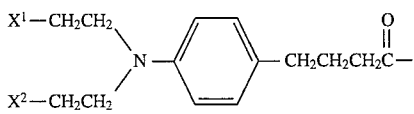

wherein both $X^1$ and $X^2$ are Cl.

In another embodiment (Formula II) the invention comprises peptides wherein the carboxy-terminal residue comprises an ethyl ester, having the following sequence (SEQ ID Nos.:11–14):

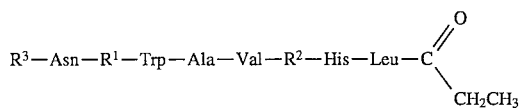

wherein $R^1$ is Gln or His, $R^2$ is Gly or D-Ala, and $R^3$, the amino terminal group, is Acetyl, Bromoacetyl, Chloroacetyl, or [bis(2-chloroethyl)amino]-L-Phe. Preferably, $R^3$ may be the chlorambucil group or a derivative thereof, i.e.,

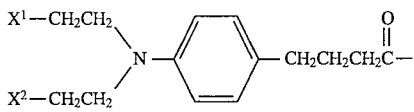

wherein $X^1$ is Cl or OH and $X^2$ is Cl or OH.

Preferable embodiments of the Formula II compounds include PTC 815 and PTC 815B in which $R^1$ is Gln, $R^2$ is D-Ala and $R^3$ is

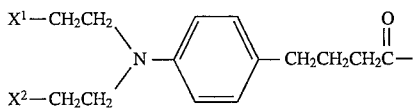

wherein $X^1$ is Cl and $X^2$ is Cl (PTC 815) or OH (PTC 815B).

The peptides of the invention may be prepared by any process well known in the art of peptide chemistry to be applicable to the synthesis of analogous compounds. Thus, for example, a peptide of the invention may be obtained by procedures analogous to those disclosed in *Solid Phase Peptide Synthesis* by Steward and Young (Pierce Chemical Company, Illinois 984), *Principles of Peptide Synthesis* (Springer-Verlag, Berlin, 1984), *Practice of Peptide Synthesis* (Springer-Verlag, Berlin, 1984), and "The Synthesis of a Tetrapeptide," *J. Chem Soc.* 83:2149 (1963).

A preferred process for synthesizing the peptides of the invention is solid-phase 9-fluoroenylmethyloxycarbonyl (FMoc) technique, according to standard methods. After drying, the peptides are extracted in water or acetic acid and lyophilized. The tert-butoxycarbonyl (Boc) derivatives of unusual amino acids are synthesized from the free amino acid. All of the terminal amino ends are acylated with large polar groups or alkylating agents such as chlorambucil or acetyl, chloroacetyl or bromoacetyl groups, in the last coupling step. The ethyl esters are generated by reacting the purified peptide with diisopropylcarbodimide in absolute ethanol. Purification of the peptides is performed using reversed-phase semi-preparative high pressure liquid chromatography (HPLC).

Another embodiment of the invention relates to a pharmaceutical composition which comprises the compounds of the invention or a pharmaceutically acceptable salt thereof, in association with a pharmaceutically acceptable diluent or carrier.

The pharmaceutical compositions utilized in this invention can be administered by intranasal, aerosol, oral, enteral, topical, sublingual, vaginal, rectal, intramuscular, intravenous, or subcutaneous means.

The compounds of this invention can be employed in combination with conventional excipients; i.e., pharmaceutically acceptable organic or inorganic carrier substances suitable for parenteral, enteral or intranasal application which do not deleteriously react with the active compounds. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. See generally, *Remington's Pharmaceutical Science,* 16th edition, Mac Eds. 1980.

For parenteral application, particularly suitable vehicles consist of solutions, preferably oily or aqueous solutions, as well as suspensions, emulsions, or implants, including suppositories. Ampules are convenient unit dosages.

A parenteral composition is preferably a solution to isotonic saline or isotonic dextrose buffered if necessary to a pH of 5 to 9. Alternatively, the parenteral composition may be one designed for slow release in which case the amount of peptide per unit dose is in general greater than that required when a conventional injectable formulation is used. A preferred slow release formulation is, for example, a continuous release formulation. A preferred slow release parenteral formulation contains from 1 to 100 mg of peptide per unit dose. Another preferred slow release formulation is a micro-encapsulated peptide using a biodegradable bicompatible copolymer. These preparations are preferably administered intravenously, although administration may also be effected by means of subcutaneous, intramuscular, or intradermal injection.

For interal application, particularly suitable are tablets, dragrees or capsules having talc and/or a carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

It will be appreciated that the actually preferred amounts of active compounds used will vary according to the specific compound being utilized, the particular compositions formulated, the mode of application and the particular site of administration. Optimal administration rates for a given protocol of administration can be readily ascertained by those skilled in the art, using conventional dosage determination tests conducted with regard to the foregoing guidelines.

According to the present invention, a "therapeutically effective amount" of a pharmaceutical composition is an amount which is sufficient to achieve the desired pharmacological effect. These effects include a BBN or GRP antagonist effect, blocking of the BBN/GRP receptor, or inhibition of the growth-promoting or other biological effects of BBN/GRP-like peptides. Generally, the dosage required to provide an effective amount of the composition, and which can be adjusted by one of ordinary skill in the art, will vary, depending upon the age, health, physical condition, sex, weight and extent of disease, of the recipient. Additionally, the dosage may be determined by the frequency of treatment and the nature and scope of the desired effect. Appropriate dosages will be determined by those of ordinary skill in the art, using routine methods. In treating cancer, particularly small cell lung carcinoma (SCLC), cultured cell lines may also be isolated from a patient and tested for dose responsiveness (Trepel et al., *Biochem. Biophys. Res. Commun.* 156:1383 (1988); Mahmoud et al., *Life Sci.* 44:367 (1989)).

In general, the above compositions may be prepared in a conventional manner using conventional excipients. However, in the case of a composition for oral administration, it may be convenient for the composition to include a coating to protect the active ingredient from the actions of enzymes in the stomach.

A composition of the invention may also contain, in addition to the peptide of the invention, one or more known anti-tumor agents selected from, among others, mitotic inhibitors, e.g., vinblastine; alkylating agents, e.g., cisplatin, carboplatin and cyclophosphamide; antimetabolites, e.g., 5-fluorouracil, cytosine arabinoside and hydroxyurea; intercalating antibiotics, e.g., adriamycin and bleomycin; enzymes, e.g., asparaginase; topoisomerase inhibitors, e.g., etoposide; biological response modifiers, e.g., interferon; and other neurogastrointestinal peptide antagonists, e.g., cholecystokinin antagonists.

A preferred composition of the invention is, for example, one suitable for oral administration in unit dosage form, for example a tablet or capsule which contains from 1 microgram to 500 mg, more preferably from 10 to 100 mg, of peptide in each unit dose, such that a daily oral dose is from 1 nanogram to 50 milligram per kg of body weight, more preferably from 0.1 to 25 mg/kg, is thereby achieved. Another preferred composition is one suitable for parenteral administration which contains from 0.5 to 100 mg of peptide per ml, more preferably from 1 to 10 mg of peptide per ml of solution, such that a daily parenteral dose of from 1 nanogram to 10 mg per kg of body weight, more preferably from 0.1 to 10 mg/kg, is thereby achieved.

Pharmaceutical compositions suitable for transdermal administration may take the form of an optionally buffered aqueous solution of the compounds of the invention and may be delivered by passive diffusion or by electrically-assisted transport, for example, iontophoresis (see, for example, *Pharmaceutical Research* 3(6):318 (1986)).

In general, the invention relates to methods in which a BBN, GRP, or BBN-like peptide antagonist effect is produced in a mammal, including humans, in need of such treatment, by administering to said mammal a therapeutically effective amount of the peptides of the invention or pharmaceutically-acceptable salts thereof. Therefore, the peptides of the invention may be used to inhibit or regulate any of the biological effects exerted by BBN/GRP-like peptides such as, for example, promoting cell growth or stimulation of the release of gastrointestinal hormones, or control of feeding behavior or hypothermia.

In one embodiment, the invention relates to a method for inhibiting the binding of BBN, GRP, or BBN/GRP-like peptides, such as neuromedins, to receptors present on cells which are capable of such binding in a mammal, including humans, by administering to the mammal the peptides of the invention (Formulas I or II) in an amount effective to inhibit the binding. Examples of such cells include those in the gastrointestinal tract, such as stomach or pancreatic, brain cells, such as those in the cerebral cortex or hypothalamus, and cancerous cells.

In a particular embodiment, the invention relates to a method for regulating processes occurring in gastrointestinal function in which BBN, GRP, or BBN/GRP-like peptides exert a biological effect. Such processes include secretion of hormones such as gastrins or those secreted from the pancreas, or cerebral control of feeding behavior, satiety, and body temperature regulation, through receptors present in the brain.

One of the important effects of BBN/GRP-peptides is the stimulation of gastrins. The gastrins stimulate hydrochloric acid and pepsinogen secretion, elevate gastric blood flow, and induce contraction of the circular smooth muscle of the stomach. Gastrins also exert a long-term trophic (growth promoting) effect on the epithelial cells of the gastric and small intestinal mucosa as well as the exocrine pancreas. Gastrins also stimulate water, bicarbonate, and electrolyte secretion by the pancreas, liver, and small intestinal mucosa in pharmacologic rather than physiologic doses. Under such conditions, gastrins also enhance enzyme secretion by the pancreas and small intestinal mucosa; inhibit gastric emptying and absorption of glucose and electrolytes by the small intestine; and promote the secretion of insulin and glucagon. Gastrins also can inhibit contraction of the pyloric sphincter, ileocecal sphincter, and hepatopancreatic ampullary sphincter. Gastrins can exert a broad range of physiologic and pharmacologic effects. However, the principal short-term action of these compounds in vivo is to stimulate hydrochloric acid secretion by the stomach, with a concomitant increase in gastric blood flow. Therefore, by inhibiting the action of BBN/GRP-like peptides, the receptor antagonists of the invention are also effective in regulating the effects of gastrin secretion.

Therefore, other conditions also include those associated with excess production of BBN or GRP, resulting in excess levels of gastrin secretion. The peptides of the invention may also be used in the treatment or prevention of conditions associated with the failure of normal physiological control of the regulation of gastric acid secretion. The production of gastrin in animals has been linked to the suppression of the release of growth hormone and prolactin. Therefore, the peptides of the invention may also be used to promote the availability of growth hormone or prolactin in mammals in need of such treatment.

Another embodiment relates to a method for treating or preventing any disease, disorder or medical condition associated with any process or effect mediated by BBN/GRP-like peptides, by administering the peptides of the invention to a mammal in need of such treatment. Examples of such conditions, diseases, or disorders will be readily ascertainable to those of skill in the medical arts using routine diagnostic methods, and include peptic ulcer, pancreatitis, eating disorders, diabetes, Zollinger-Ellison syndrome, acromegaly, enterocutaneous fistula, psoriasis, postoperative small bowel fistula, dumping syndrome, anorexia, growth retardation, and gastrointestinal motility disorders.

A particularly significant aspect of this embodiment is a method for inhibiting the growth of cancerous cells or tumors by administering to a mammal, an amount of any of the peptides of the invention sufficient to inhibit the growth of cancerous cells. The inventors have demonstrated that the peptides of the invention are highly potent in inhibiting the growth of cancerous cells such as SCLC. Therefore, the peptides of the invention may be administered to a mammal for the treatment or prevention of cancerous disease. Examples of such cancerous disease includes any type of cancer in which the cells contain receptors or BBN/GRP-like peptides, or in which such peptides exert a growth-promoting effect. In particular, types of disease include, but are not limited to cancers of the lung, brain, stomach, pancreas, skin, pituitary, breast, prostate, and adrenal glands, including for example, SCLC, gastrinoma, neuroblastoma, exocrine pancreatic adenocarcinoma, pancreatic islet carcinoma and pituitary growth hormone cell adenoma.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

The entire text of all publications cited above and below are hereby incorporated by reference.

EXAMPLES

Structures of Bombesin Receptor Antagonists

Table 1 lists the abbreviations used herein to designate amino acids residues present in the structures of the Bombesin receptor antagonists.

The chemical structures of the BBN analogs prepared and screened for antagonist activity are shown in FIG. 1 (cyclic analogs) and FIG. 2 (linear analogs).

TABLE 1

Abbreviations for Amino Acids

| Amino Acid | Abbreviation |
| --- | --- |
| Alanine | Ala |
| Dextrorotatory Alanine | D-Ala |
| Arginine | Arg |
| Asparagine | Asn |
| Aspartic acid | Asp |
| Cysteine | Cys |
| Glutamine | Gln |
| Glutamic acid | Glu |
| Pyroglutamic acid | pGlu |
| Glycine | Gly |
| Histidine | His |
| Isoleucine | Ile |
| Leucine | Leu |
| Lysine | Lys |
| Dextrorotatory Lysine | D-Lys |
| Methionine | Met |
| Methionine amide | Met-NH$_2$ |
| Phenylalanine | Phe |
| Proline | Pro |
| Serine | Ser |
| Threonine | Thr |
| Tryptophan | Trp |
| Tyrosine | Tyr |
| Valine | Val |

Synthesis of Bombesin Receptor Antagonists

Chemical Peptide Synthesis

The peptides were synthesized by solid-phase techniques (Stewart and Young, *Solid Phase Peptide Synthesis*, Pierce Chemical Co., Rockland, Ill. (1985)) the Biosearch 9600AT synthesizer using a standard Fmoc protocol. Most of the peptides were assembled via the Fmoc chemistry starting with Fmoc Leu hydroxybenzyl alcohol resin (Wang resin). Each Fmoc protected amino acid including the im Trityl His and e-butyl-D-Lys and Trityl Asn and Gln derivatives were coupled with PyBOP benzotriazolyloxytris (pyrollidyl) phosphonium hexafluorophosphate) and hydroxybenzotriazole (HOBt) and N-methylmorpholine which forms the highly efficient benzotriazolyl active ester. The Fmoc group was deprotected with 20% piperidine prior to the coupling. The peptide was cleaved and side groups deprotected by reaction with trifluoroacetic acid (TFA) in the presence of scavengers such as anisole, thioanisole, and ethanedithiol.

After drying, the peptides were extracted in water or acetic acid and lyophilized. The Boc derivatives of unusual amino acids were synthesized from the free amino acid. All of the terminal amino ends were acylated with compounds such as acetyl, bromoacetyl or chloroacetyl groups, or chlorambucil, in the last coupling step. The ethyl esters were generated by reacting the purified peptide with diisopropylcarbodiimide in absolute ethanol.

Peptide Purification

The peptides were purified by reversed-phase semi-preparative HPLC on a C$_{18}$ S-10, 2.2×30-cm column (YMC, Inc.) in 0.1% aqueous TFA with acetonitrile gradients. The eluent containing pure peptide was freeze-dried to a fluffy powder in yields of 10 to 60 mg. Amino acid analysis was performed by ion exchange HPLC chromatography (St. John's Associates) with post-column o-phlalaldehyde fluorescence detection. The peptides were also analyzed by fast atom bombardment spectrometry.

Biological Activity of Bombesin Receptor Antagonists

Outline of the Strategy Used to Identify Useful Antagonists

In order to evaluate biological activities of compounds derived from the structures of BBN or GRP, biological systems known to be responsive to BBN and/or GRP were used. Because compounds which act as BBN/GRP antagonists in one system may also act as partial agonists in other systems (Coy et al., *Eur. J. Phramacol.* 190:31 (1990)), several biological systems were employed.

Acinar cells from rat pancreas bind BBN and secrete amylase when treated with BBN. The ability of potential antagonists to bind to rat pancreatic acinar cells was examined by determining the ability of the compounds to inhibit the binding of radiolabelled BBN. Potential agonist effects were ruled out by demonstrating that the compounds, by themselves, do not stimulate the release of amylase from rat pancreatic acinar cells. Finally, antagonist activity of the compounds was determined by measuring the ability of compounds to prevent the release of amylase from cells in response to BBN. A human tumor cell line, NCI-H345, derived from a patient with small cell lung carcinoma (SCLC) is known to bind BBN and exhibits increased mitogenic growth when exposed to BBN (Mahmoud et al., *Cancer Res.* 51:1798 (1991)). This cell line was also used to evaluate biological activities of potential antagonists derived from the structures of BBN and GRP. The binding of synthetic compounds to cellular membranes prepared from NCI-H345 was determined. The ability of potential antagonists to block the BBN-stimulated increase in cytosolic levels of Ca$^{++}$ was determined. Compounds showing inhibition were further tested to determine the effect on growth of two human SCLC cell lines in culture.

Pancreatic Acinar Cell Function

Dispersed acinar cells from rat pancreas were prepared by digestion with collagenase and washed. The cells were incubated and washed with the standard solution containing 25.5 mM HEPES, pH 7.4, 98 mM NaCl, 6 mM KCl, 2.5 mM NaH$_2$PO$_4$, 5 mM Na Pyruvate, 5 MM Na fumarate, 5 mM Na fumarate, 5 mM Na glummate, 11.5 mM glucose, 0.5 mM CaCl$_2$, 1.0 mM MgCl$_2$, 2 mM Gln, 0.01% (w/v) trypsin inhibitor, 1% v/v vitamin mixture and 1% amino acid mixture. The incubation solution contained 1% albumin and the wash solution contained 0.2% albumin. The solution was equilibrated with 100% O$_2$. Dispersed acini were suspended in 20 ml of solution. Samples of 1 ml were incubated in the presence of various concentrations of compounds in the presence of 1 nM bombesin. After the first incubation the samples were washed 4 times with wash solution at 4° C. The acini were then resuspended in fresh incubation buffer and incubated at 37° C. Amylase release was measured by the Phadebas reagent. Amylase secretion during a given incubation was expressed as the percentage of amylase present in the acini at the beginning of that incubation that was released into the extracellular medium.

Inhibition of equilibrium binding of $^{125}$I labeled bombesin to acinar membranes by the compounds was determined. The K$_d$ was determined by dividing IC$_{50}$ (the concentration of synthetic compound required to inhibit 50% of the specific binding of labelled BBN) by the concentration of radiolabeled peptide.

Reversibility Assay

Dispersed acinar cells from rat pancreas were prepared as indicated above. The cells were incubated with or without antagonist (1 μM) for 30 minutes, washed with buffer, and then resuspended in fresh buffer that included BBN (1 nM). Aliquots were taken 1, 30, or 60 minutes and levels of amylase, secreted by the cells in response to BBN, were measured.

In order to evaluate the specificity of antagonists for BBN receptors, parallel experiments were performed in which the cells were incubated with antagonist and washed as described above, and then were resuspended in fresh buffer that contained cholecystokinin (CCK) (0.1 nM) instead of BBN. CCK is a peptide which stimulates amylase secretion but is not a member of the BBN/GRP family of peptides. CCK acts on cells via a receptor other than the BBN receptor. Thus, inhibition of BBN-stimulated, but not CCK-stimulated, amylase secretion indicates that an antagonist is specific for BBN receptors.

Cytosolic Ca$^{++}$ Assay

SCLC cell line NCI-H345 was cultured for two days in medium containing 10$^{-8}$M hydrocortisone, 5 μg/ml bovine insulin, 10 μg/ml human transferrin, 10$^{-8}$M β-estradiol and 3×10$^{-8}$M Na$_2$SeO$_3$. The cells were harvested and washed, resuspended in medium containing 20 mM HEPES, pH 7.4, and loaded with 5 +82M Fura 2 AM (Calbiochem) for 30 minutes. The cells were centrifuged at 150×g for 10 minutes to remove extracellular dye and resuspended and placed in a spectrofluorometer cell equipped with stirring and 37° C. heating. The emission was read at 510 nm with 340 excitation (Moody et al., *Biochem. Biophys. Res. Commun.* 147:189 (1987)). The response of compounds at 5 +82M was measured initially as a screen and compared to that of 10 nM BBN. The response of varying concentrations of peptide (nM to μM) in the presence of 10 nM BBN was determined.

Clonagenic Assay

The effect of 1 to 1000 nM concentration of peptides on growth of NCI-H345 colonies stimulated by 10 nM BBN was measured in the agarose cloning system (Mahoud et al., *Cancer Res.* 51:1798 (1991); Staley et al., *Peptides* 12:145–149 (1991)). The human SCLC cell line NCI-H345 was cultured in serum-supplemented medium (RMI 1640) in a humidified atmosphere of 5% CO$_2$ and 95% air at 37° C.

On the day of the assay, cells were harvested, centrifuged and suspended in the buffer. The agarose cloning system consisted of 3 ml of 0.5% agarose in SIT medium with 5% fetal bovine serum in six well plates. To a top layer, consisting of 3 ml HITES medium in 0.3% agarose, the peptides at two times concentration and 6×10$^4$ single viable cells, were added. For each peptide concentration, triplicate wells were plated. After two weeks, 1 ml of 0.1% p-iodonitrotetrazolium violet was added, and after 16 hours at 37° C., the plates were screened for colony formation; the number of colonies larger than 120 +82M in diameter were counted using a Bausch and Lomb Omnicon image analysis system.

Results

The ability of the synthetic compounds to bind to rat pancreatic acinar cells, and to stimulate or inhibit the release of amylase therefrom, is shown in Table 2. None of the synthetic compounds had agonistic activity in this assay (column 1). Many of the compounds apparently do not bind to rat pancreatic acinar cells (column 3), although PTC 815, PTC 818 and PTC 821 did bind to the cells, as demonstrated by their ability to inhibit the binding of radiolabelled BBN. Antagonist activity (column 2) tracks binding activity, as the compound showing the most affinity for the BBN receptor on the cells (PTC 821) also demonstrates the most potent antagonistic effect. Strikingly, two compounds (PTC 815 and PTC 821), although having different sequences, were both potent antagonists. Both PTC 815 and PTC 821 have an amino terminal chlorambucil group.

TABLE 2

Potencies of Bombesin Receptor Antagonists on Rat Pancreatic Acinar Cell Function

| Compound | 1. E.C.$_{50}$ (nM) | 2. I.C.$_{50}$ (nM) | 3. K$_d$ (nM) |
|---|---|---|---|
| PTC 803 | >3000 | >3000 | >3000 |
| PTC 804 | >3000 | >3000 | >3000 |
| PTC 805 | >3000 | >3000 | >3000 |
| PTC 806 | >3000 | >3000 | >3000 |
| PTC 807 | >3000 | >3000 | >3000 |
| PTC 808 | >3000 | >3000 | >3000 |
| PTC 809 | >3000 | >3000 | >3000 |
| PTC 815 | >3000 | 8.5 ± 0.5 | 10.7 ± 3.4 |
| PTC 818 | >3000 | 4.9 ± 0.1 | 8.1 ± 1.8 |
| PTC 820 | >3000 | >3000 | >3000 |
| PTC 821 | >3000 | 6.3 ± 0.9 | 3.2 ± 0.5 |

As shown in column 1, all compounds had no agonist activity (E.C.$_{50}$ values >3000 nM). In column 2, the concentration of half-maximal inhibition (mean ± s.e.m.) of nM bombesin-stimulated release of amylase from acini is given. The values in column 3 represent the ability of the compounds to bind to cells, determined by inhibition of $^{125}$I bombesin binding.

Potential antagonists were also evaluated for their ability to inhibit the binding of radiolabelled Tyr$^4$-BBN to SCLC membranes and for their effects on BBN signal transduction in SCLC cells. As shown in Table 3 (column 1), many compounds do not bind SCLC membranes, and PTC 804 and PCT 812 exhibit only weak inhibition of BBN binding. However, several compounds, (PTC 815, 815B, 816, 818 and 821) are potent inhibitors of BBN binding. The latter five compounds also inhibit the effect of BBN to increase cytosolic Ca$^{++}$ concentrations (column 2) and significantly reduce clonal growth of the SCLC cells (column 3; PTC 821 was not evaluated in this assay).

TABLE 3

Potency of Bombesin receptor antagonists on SCLC cell line NCI-H345

| Peptide | 1. IC$_{50}$(nM) | 2. Ca$^{++}$ effect | 3. Growth |
|---|---|---|---|
| PTC 803 | >10000 | — | n.d. |
| PTC 804 | 6000 | — | n.d. |
| PTC 805 | >10000 | — | n.d. |
| PTC 807 | >10000 | — | n.d. |
| PTC 808 | >10000 | — | n.d. |
| PTC 809 | >10000 | — | n.d. |
| PCT 812 | 4000 | A | R |
| PCT 815 | 35 | A | R |
| PTC 815B | 45 | A | n.d. |
| PTC 816 | 55 | A | R |
| PTC 818 | 25 | A | R |
| PTC 820 | >10000 | — | — |
| PTC 821 | 8 | A | n.d. |

The concentration of synthetic compound required to inhibit 50% of the specific[$^{125}$I]Tyr$^4$-BBN binding (IC$_{50}$) is indicated in column 1. The data in column 2 indicate whether the compounds (10 μM) antagonized (A) or had no effect (—) on the ability of 10 nM BBN to elevate cytosolic Ca$^{++}$. The data in column 3 indicate whether the compounds (1 μM) significantly reduced (R) or had no effect (—) on the clonal growth of a human tumor cell line; n.d., not determined.

The more potent compounds identified in the experiments were then evaluated for their effects on clonal cell growth of two human SCLC cell lines, NCI-H345 and NCI-H270. As shown in Table 4, PTC 815, PTC 818 and PTC 816 reduce the amount of colony formation by both cell lines (compare lines 2, 3 and 4, respectively, with line 1). The inhibition resulting from 1 +82M PTC 818 or PTC 816 can be reversed by the addition of an excess (10 nM) of BBN. This demonstrates that the compounds are competing with BBN for cellular receptors and that they exert their effects through these receptors. The ability of the bombesin receptor antagonists to inhibit the clonal growth of two unrelated SCLC call lines indicates the broad applicability of the antagonists to SCLC tumors.

TABLE 4

Effect on colony formation of Bombesin receptor positive cell lines by Bombesin receptor antagonists

| Addition | NCI-H345 | NCI-H720 |
|---|---|---|
| None | 48 ± 4 | 50 ± 4 |
| PTC 815 1 μM | 38 ± 4* | 33 ± 1** |
| PTC 818 1 μM | 20 ± 5* | 36 ± 4** |
| PTC 816 1 μM | 27 ± 4* | 37 ± 6 |
| BBN 10 nM | 111 ± 1** | 125 ± 4** |
| BBN + PTC 818 | 57 ± 6 | 62 ± 7 |
| BBN + PTC 816 | 52 ± 3 | 66 ± 8 |

Colony per mm$^2$. The mean value ± S.E. of 3 determinations is indicated; *p < 0.05; **p < 0.01.

Finally, the most potent antagonist identified by the above experiments, PTC 821, was examined to determine the ability of BBN to reverse the antagonist effect and the length of time required by rat pancreatic acinar cells to recover from its inhibitory effect. As shown in Table 5, addition of 1 nM BBN only partially reversed the inhibitory effect of PTC 821. Only 25% of the cells'BBN receptor activity reappeared 60 minutes after incubation with, and removal of, PTC 821. In order for such an extended period of receptor inhibition to occur, PTC 821 must be stable in the appropriate cellular microenvironment. Moreover, PTC 821 probably forms a stable and tight complex with the BBN receptor, as the effect persists for 60 minutes and most of the PTC 821 molecules are apparently not displaced by a fresh solution containing an excess of BBN.

It is important to note that the inhibitory effect of PTC 821 was specific for BBN and did not affect the cells' response to CCK-stimulated amylase secretion. Moreover, no changes in the appearance of the cells, indicative of toxicity of the compound, were observed.

TABLE 5

Reversibility of the action of PTC 821 on Pancreatic Acinar Cell Secretion Amylase Release (% Total)

| Antiagonist | Secretion (Wash) | Determination of Secretion Post-Wash | | |
|---|---|---|---|---|
| | | 1 Min | 30 Min | 60 Min |
| None | | | | |
| control | 3.3 ± 0.4 | 2.4 ± 0.5 | 2.1 ± 0.6 | 2.5 ± 0.4 |
| BBN, 1 nM | 14.1 ± 1.5 | 10.6 ± 1.8 | 9.1 ± 1.4 | 7.7 ± 2.1 |
| CCK, 0.1 nM | 16.4 ± 1.9 | 12.6 ± 1.7 | 8.2 ± 1.0 | 9.3 ± 2.0 |
| PTC 821, 1 μM | | | | |
| control | 3.6 ± 0.4 | 3.0 ± 0.7 | 1.7 ± 0.3 | 2.9 ± 0.4 |
| BBN, 1 nM | 2.3 ± 0.2 | 3.4 ± 0.7 | 2.8 ± 0.5 | 4.2 ± 1.90 |
| CCK, 0.1 nM | 14.8 ± 1.9 | 13.9 ± 1.6 | 8.7 ± 1.0 | 10.5 ± 2.2 |
| Percent BBN Receptor Activity Recovered: | | 5% | 18% | 25% |
| Percent CCK Receptor Activity Recovered: | | 107% | 115% | 89% |

These experiments demonstrate potent inhibitory analogs of BBN and GRP that have a long-lasting effect in vitro. The bombesin receptor antagonists described herein can be used to inhibit the in vivo effects that are promoted by GRP and other BBN-related peptides.

What is claimed is:

1. A synthetic derivative of a peptide having
   (a) an amino terminal chlorambucil group,

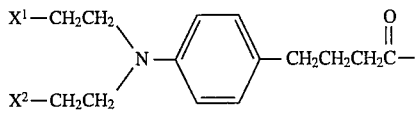

wherein $X^1$ is Cl or OH and $X^2$ is Cl or OH; and
   (b) a peptide sequence derived from that of bombesin (SEQ ID No.:1), gastrin releasing peptide (SEQ ID No.:15), Neuromedin B (SEQ ID No.:16) or Neuromedin C (SEQ ID No.:2).

2. A bombesin receptor antagonist that is a peptide, wherein the carboxy-terminal residue of said peptide has an ethyl ester, and said peptide has the sequence $R^4$-His-Trp-Ala-$R^1$-$R^2$-His-$R^3$, wherein is Val or Thr, $R^2$ is Gly or D-Ala, $R^3$ is Leu, ethyl ester or Phe, ethyl ester and $R^4$ is N-Acetyl, Bromoacetyl, Chloroacetyl, (bis(2-chloroethyl)amino)-L-phenylalanine, or

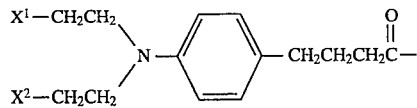

wherein $X^1$ is Cl or OH and $X^2$ is Cl or OH (SEQ ID Nos.:3–10).

3. The bombesin receptor antagonist of claim 2, wherein $R^1$ is Val, $R^2$ is D-Ala, $R^3$ is Leu, and $R^4$ is

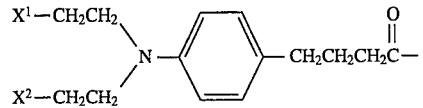

wherein $X^1$ is Cl or OH and $X^2$ is Cl or OH (SEQ ID No.:5).

4. The bombesin receptor antagonist of claim 3, wherein both $X^1$ and $X^2$ are Cl.

5. The bombesin receptor antagonist of claim 2, wherein $R^1$ is Val, $R^2$ is D-Ala, $R^3$ is Leu and $R^4$ is an Acetyl group (SEQ ID No.:5).

6. A bombesin receptor antagonist that is a peptide, wherein the carboxy-terminal residue of said peptide has an ethyl ester, and said peptide has the sequence $R^3$-Asn-$R^1$-Trp-Ala-Val-$R^2$-His-Leu, ethyl ester, wherein $R^1$ is Gln or His, $R^2$ is Gly or D-Ala and $R^3$ is N-Acetyl, Bromoacetyl, Chloroacetyl, (bis(2-chloroethyl)amino)-L-phenylalanine, or

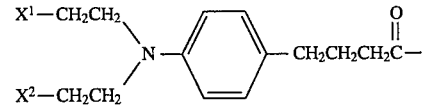

wherein $X^1$ is Cl or OH and $X^2$ is Cl or OH (SEQ ID Nos.:11–14).

7. The bombesin receptor antagonist of claim 6, wherein $R^1$ is Gln, $R^2$ is D-Ala, and $R^3$ is

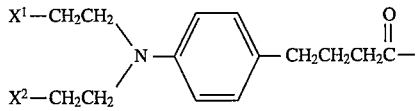

wherein $X^1$ is Cl or OH and $X^2$ is Cl or OH (SEQ ID No.:12).

8. The bombesin receptor antagonist of claim 7, wherein $X^1$ is OH and $X^2$ is Cl.

9. The bombesin receptor antagonist of claim 7, wherein both $X^1$ and $X^2$ are Cl.

10. A pharmaceutical composition comprising the bombesin receptor antagonist of any one of claims 1–9 and a pharmaceutically acceptable carrier.

11. A method of inhibiting the growth of small cell lung cancer or pancreatic cells that are sensitive to the growth-promoting effect of bombesin or gastrin releasing peptide which comprises treating the cells with the bombesin receptor antagonist of any one of claims 1–9 in an amount effective to inhibit the growth-promoting effects of bombesin.

12. A method for inhibiting the growth of small cell lung cancer or pancreatic cells that are sensitive to the growth-promoting effect of bombesin, gastrin releasing peptide neuromedin B or neuromedin C in a mammal which comprises the administration to said mammal of a therapeutically effective amount of the pharmaceutical composition of claim 10.

13. A method for inhibiting the binding of bombesin, gastrin releasing peptide neuromedin B or neuromedin C to small cell lung cancer or pancreatic cells capable of said binding which comprises treating said cells with an effective amount of the bombesin receptor antagonist of any one of claims 1–9.

14. A method for inhibiting the binding of bombesin, gastrin releasing peptide neuromedin B or neuromedin C to small cell lung cancer or pancreatic cells capable of said binding in a mammal, which comprises the administration to said mammal of the pharmaceutical composition of claim 10 in an amount effective to inhibit said binding.

15. The method of claim 14 wherein said mammal is a human.

16. A method for treating small cell lung cancer in a mammal, which comprises the steps of
    (a) isolating and culturing a cell line from a tumor in said mammal;
    (b) determining if the cultured cell line of (a) undergoes a mitogenic response when treated with bombesin; and, if so,
    (c) administering to said mammal an effective amount of the pharmaceutical composition of claim 10.

17. The method of claim 16, wherein said mammal is a human.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 14 amino acids
( B ) TYPE: amino acid ( D ) TOPOLOGY: linear ( i i ) MOLECULE TYPE: peptide ( v i ) ORIGINAL SOURCE:
            ( A ) ORGANISM: Bombina bombina ( i x ) FEATURE:
            ( A ) NAME/KEY: Modified-site
            ( B ) LOCATION: 1
            ( D ) OTHER INFORMATION: /note="The glutamic acid at
                    position 1 is pyroglutamic acid."

( i x ) FEATURE:
            ( A ) NAME/KEY: Modified-site
            ( B ) LOCATION: 14
            ( D ) OTHER INFORMATION: /note="The methionine at position
                    14 is methionine amide."

( x ) PUBLICATION INFORMATION:
            ( A ) AUTHORS: Erspamer, V.
            ( B ) TITLE: Discovery, Isolation, and Characterization of
                    Bombesin- like Peptides
            ( C ) JOURNAL: Ann. N. Y. Acad. Sci.
            ( D ) VOLUME: 547
            ( F ) PAGES: 3-9
            ( G ) DATE: 1988
            ( K ) RELEVANT RESIDUES IN SEQ ID NO:1: FROM 1 TO 14

( x i ) SEQUENCE DESCRIPTION: SEQ ID NO:1:

Glu  Gln  Arg  Leu  Gly  Asn  Gln  Trp  Ala  Val  Gly  His  Leu  Met
    1                   5                        10

( 2 ) INFORMATION FOR SEQ ID NO:2:

( i ) SEQUENCE CHARACTERISTICS:
            ( A ) LENGTH: 10 amino acids
            ( B ) TYPE: amino acid
            ( D ) TOPOLOGY: linear ( i i ) MOLECULE TYPE: peptide ( v i ) ORIGINAL SOURCE:
            ( A ) ORGANISM: Pig ( i x ) FEATURE:
            ( A ) NAME/KEY: Modified-site
            ( B ) LOCATION: 10
            ( D ) OTHER INFORMATION: /note="The methionine at position
                    10 is methionine amide."

( x ) PUBLICATION INFORMATION:
            ( A ) AUTHORS: Erspamer, V.
            ( B ) TITLE: Discovery, Isolation, and Characterization of
                    Bombesin- like Peptides
            ( C ) JOURNAL: Ann. N. Y. Acad. Sci.
            ( D ) VOLUME: 547
            ( F ) PAGES: 3-9
            ( G ) DATE: 1988
            ( K ) RELEVANT RESIDUES IN SEQ ID NO:2: FROM 1 TO 10

( x i ) SEQUENCE DESCRIPTION: SEQ ID NO:2:

Gly  Asn  His  Trp  Ala  Val  Gly  His  Leu  Met
    1                   5                        10

( 2 ) INFORMATION FOR SEQ ID NO:3:

( i ) SEQUENCE CHARACTERISTICS:
            ( A ) LENGTH: 7 amino acids
            ( B ) TYPE: amino acid
            ( D ) TOPOLOGY: linear ( i x ) FEATURE:
            ( A ) NAME/KEY: Modified-site
            ( B ) LOCATION: 1
            ( D ) OTHER INFORMATION: /note="The amino-terminal residue comprises one of several chemical end caps."

( i x ) FEATURE:
  ( A ) NAME/KEY: Modified-site
  ( B ) LOCATION: 7
  ( D ) OTHER INFORMATION: /note="The carboxy-terminal
        residue comprises an ethyl ester."

( x i ) SEQUENCE DESCRIPTION: SEQ ID NO:3:

His  Trp  Ala  Val  Gly  His  Leu
1                   5

( 2 ) INFORMATION FOR SEQ ID NO:4:

( i ) SEQUENCE CHARACTERISTICS:
    ( A ) LENGTH: 7 amino acids
    ( B ) TYPE: amino acid
    ( D ) TOPOLOGY: linear ( i x ) FEATURE:
    ( A ) NAME/KEY: Modified-site
    ( B ) LOCATION: 1
    ( D ) OTHER INFORMATION: /note="The amino-terminal residue
          comprises one of several chemical end caps."

( i x ) FEATURE:
    ( A ) NAME/KEY: Modified-site
    ( B ) LOCATION: 7
    ( D ) OTHER INFORMATION: /note="The carboxy-terminal
          residue comprises an ethyl ester."

( x i ) SEQUENCE DESCRIPTION: SEQ ID NO:4:

His  Trp  Ala  Thr  Gly  His  Leu
1                   5

( 2 ) INFORMATION FOR SEQ ID NO:5:

( i ) SEQUENCE CHARACTERISTICS:
    ( A ) LENGTH: 7 amino acids
    ( B ) TYPE: amino acid
    ( D ) TOPOLOGY: linear ( i x ) FEATURE:
    ( A ) NAME/KEY: Modified-site
    ( B ) LOCATION: 1
    ( D ) OTHER INFORMATION: /note="The amino-terminal residue
          comprises one of several chemical end caps."

( i x ) FEATURE:
    ( A ) NAME/KEY: Modified-site
    ( B ) LOCATION: 5
    ( D ) OTHER INFORMATION: /note="The alanine at position 5
          is dextrorotatory alanine."

( i x ) FEATURE:
    ( A ) NAME/KEY: Modified-site
    ( B ) LOCATION: 7
    ( D ) OTHER INFORMATION: /note="The carboxy-terminal
          residue comprises an ethyl ester."

( x i ) SEQUENCE DESCRIPTION: SEQ ID NO:5:

His  Trp  Ala  Val  Ala  His  Leu
1                   5

( 2 ) INFORMATION FOR SEQ ID NO:6:

( i ) SEQUENCE CHARACTERISTICS:
    ( A ) LENGTH: 7 amino acids
    ( B ) TYPE: amino acid
    ( D ) TOPOLOGY: linear ( i x ) FEATURE:
    ( A ) NAME/KEY: Modified-site
    ( B ) LOCATION: 1

(D) OTHER INFORMATION: /note="The amino-terminal residue
            comprises one of several chemical end caps."

( i x ) FEATURE:
        (A) NAME/KEY: Modified-site
        (B) LOCATION: 5
        (D) OTHER INFORMATION: /note="The alanine at position 5
            is dextrorotatory alanine."

( i x ) FEATURE:
        (A) NAME/KEY: Modified-site
        (B) LOCATION: 7
        (D) OTHER INFORMATION: /note="The carboxy-terminal
            residue comprises an ethyl ester."

( x i ) SEQUENCE DESCRIPTION: SEQ ID NO:6:

His   Trp   Ala   Thr   Ala   His   Leu
    1                       5

(2) INFORMATION FOR SEQ ID NO:7:

( i ) SEQUENCE CHARACTERISTICS:
        (A) LENGTH: 7 amino acids
        (B) TYPE: amino acid
        (D) TOPOLOGY: linear ( i x ) FEATURE:
        (A) NAME/KEY: Modified-site
        (B) LOCATION: 1
        (D) OTHER INFORMATION: /note="The amino-terminal residue
            comprises one of several chemical end caps."

( i x ) FEATURE:
        (A) NAME/KEY: Modified-site
        (B) LOCATION: 7
        (D) OTHER INFORMATION: /note="The carboxy-terminal
            residue comprises an ethyl ester."

( x i ) SEQUENCE DESCRIPTION: SEQ ID NO:7:

His   Trp   Ala   Val   Gly   His   Phe
    1                       5

(2) INFORMATION FOR SEQ ID NO:8:

( i ) SEQUENCE CHARACTERISTICS:
        (A) LENGTH: 7 amino acids
        (B) TYPE: amino acid
        (D) TOPOLOGY: linear ( i x ) FEATURE:
        (A) NAME/KEY: Modified-site
        (B) LOCATION: 1
        (D) OTHER INFORMATION: /note="The amino-terminal residue
            comprises one of several chemical end caps."

( i x ) FEATURE:
        (A) NAME/KEY: Modified-site
        (B) LOCATION: 7
        (D) OTHER INFORMATION: /note="The carboxy-terminal
            residue comprises an ethyl ester."

( x i ) SEQUENCE DESCRIPTION: SEQ ID NO:8:

His   Trp   Ala   Thr   Gly   His   Phe
    1                       5

(2) INFORMATION FOR SEQ ID NO:9:

( i ) SEQUENCE CHARACTERISTICS:
        (A) LENGTH: 7 amino acids
        (B) TYPE: amino acid
        (D) TOPOLOGY: linear ( i x ) FEATURE:
        (A) NAME/KEY: Modified-site (B) LOCATION: 1
            (D) OTHER INFORMATION: /note="The amino-terminal residue
                comprises one of several chemical end caps."

(ix) FEATURE:
            (A) NAME/KEY: Modified-site
            (B) LOCATION: 5
            (D) OTHER INFORMATION: /note="The alanine at position 5
                is dextrorotatory alanine."

(ix) FEATURE:
            (A) NAME/KEY: Modified-site
            (B) LOCATION: 7
            (D) OTHER INFORMATION: /note="The carboxy-terminal
                residue comprises an ethyl ester."

(xi) SEQUENCE DESCRIPTION: SEQ ID NO:9:

His  Trp  Ala  Val  Ala  His  Phe
    1                   5

(2) INFORMATION FOR SEQ ID NO:10:

(i) SEQUENCE CHARACTERISTICS:
            (A) LENGTH: 7 amino acids
            (B) TYPE: amino acid
            (D) TOPOLOGY: linear (ix) FEATURE:
            (A) NAME/KEY: Modified-site
            (B) LOCATION: 1
            (D) OTHER INFORMATION: /note="The amino-terminal residue
                comprises one of several chemical end caps."

(ix) FEATURE:
            (A) NAME/KEY: Modified-site
            (B) LOCATION: 5
            (D) OTHER INFORMATION: /note="The alanine at position 5
                is dextrorotatory alanine."

(ix) FEATURE:
            (A) NAME/KEY: Modified-site
            (B) LOCATION: 7
            (D) OTHER INFORMATION: /note="The carboxy-terminal
                residue comprises an ethyl ester."

(xi) SEQUENCE DESCRIPTION: SEQ ID NO:10:

His  Trp  Ala  Thr  Ala  His  Phe
    1                   5

(2) INFORMATION FOR SEQ ID NO:11:

(i) SEQUENCE CHARACTERISTICS:
            (A) LENGTH: 8 amino acids
            (B) TYPE: amino acid
            (D) TOPOLOGY: linear (ix) FEATURE:
            (A) NAME/KEY: Modified-site
            (B) LOCATION: 1
            (D) OTHER INFORMATION: /note="The amino-terminal residue
                comprises one of several chemical end caps."

(ix) FEATURE:
            (A) NAME/KEY: Modified-site
            (B) LOCATION: 8
            (D) OTHER INFORMATION: /note="The carboxy-terminal
                residue comprises an ethyl ester."

(xi) SEQUENCE DESCRIPTION: SEQ ID NO:11:

Asn  Gln  Trp  Ala  Val  Gly  His  Leu
    1                   5

(2) INFORMATION FOR SEQ ID NO:12:

( i ) SEQUENCE CHARACTERISTICS:
   ( A ) LENGTH: 8 amino acids
   ( B ) TYPE: amino acid
   ( D ) TOPOLOGY: linear ( i x ) FEATURE:
   ( A ) NAME/KEY: Modified-site
   ( B ) LOCATION: 1
   ( D ) OTHER INFORMATION: /note="The amino-terminal residue
         comprises one of several chemical end caps."

( i x ) FEATURE:
   ( A ) NAME/KEY: Modified-site
   ( B ) LOCATION: 6
   ( D ) OTHER INFORMATION: /note="The alanine at position 6
         is dextrorotatory alanine."

( i x ) FEATURE:
   ( A ) NAME/KEY: Modified-site
   ( B ) LOCATION: 8
   ( D ) OTHER INFORMATION: /note="The carboxy-terminal
         residue comprises an ethyl ester."

( x i ) SEQUENCE DESCRIPTION: SEQ ID NO:12:

Asn Gln Trp Ala Val Ala His Leu
1               5

( 2 ) INFORMATION FOR SEQ ID NO:13:

( i ) SEQUENCE CHARACTERISTICS:
      ( A ) LENGTH: 8 amino acids
      ( B ) TYPE: amino acid
      ( D ) TOPOLOGY: linear ( i x ) FEATURE:
      ( A ) NAME/KEY: Modified-site
      ( B ) LOCATION: 1
      ( D ) OTHER INFORMATION: /note="The amino-terminal residue
            comprises one of several chemical end caps."

( i x ) FEATURE:
      ( A ) NAME/KEY: Modified-site
      ( B ) LOCATION: 8
      ( D ) OTHER INFORMATION: /note="The carboxy-terminal
            residue comprises an ethyl ester."

( x i ) SEQUENCE DESCRIPTION: SEQ ID NO:13:

Asn His Trp Ala Val Gly His Leu
1               5

( 2 ) INFORMATION FOR SEQ ID NO:14:

( i ) SEQUENCE CHARACTERISTICS:
      ( A ) LENGTH: 8 amino acids
      ( B ) TYPE: amino acid
      ( D ) TOPOLOGY: linear ( i x ) FEATURE:
      ( A ) NAME/KEY: Modified-site
      ( B ) LOCATION: 1
      ( D ) OTHER INFORMATION: /note="The amino-terminal residue
            comprises one of several chemical end caps."

( i x ) FEATURE:
      ( A ) NAME/KEY: Modified-site
      ( B ) LOCATION: 6
      ( D ) OTHER INFORMATION: /note="The alanine at position 6
            is dextrorotatory alanine."

( i x ) FEATURE:
      ( A ) NAME/KEY: Modified-site
      ( B ) LOCATION: 8
      ( D ) OTHER INFORMATION: /note="The carboxy-terminal
            residue comprises an ethyl ester."

( x i ) SEQUENCE DESCRIPTION: SEQ ID NO:14:

```
         Asn His Trp Ala Val Ala His Leu
         1               5
```

( 2 ) INFORMATION FOR SEQ ID NO:15:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Homo sapiens ( i x ) FEATURE:
        ( A ) NAME/KEY: Modified-site
        ( B ) LOCATION: 27
        ( D ) OTHER INFORMATION: /note="The methionine at position
                27 is methionine amide."

( x ) PUBLICATION INFORMATION:
        ( A ) AUTHORS: Spindel, Eliot R.
                Krane, Ian M.
        ( B ) TITLE: Molecular Biology of Bombesin-like Peptides
        ( C ) JOURNAL: Ann. N. Y. Acad. Sci.
        ( D ) VOLUME: 547
        ( F ) PAGES: 10-20
        ( G ) DATE: 1988
        ( K ) RELEVANT RESIDUES IN SEQ ID NO:2: FROM 1 TO 27

( x i ) SEQUENCE DESCRIPTION: SEQ ID NO:15:

```
Val Pro Leu Pro Ala Gly Gly Gly Thr Val Leu Thr Lys Met Tyr Pro
1               5                   10                  15

Arg Gly Asn His Trp Ala Val Gly His Leu Met
                20              25
```

( 2 ) INFORMATION FOR SEQ ID NO:16:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Homo sapiens ( i x ) FEATURE:
        ( A ) NAME/KEY: Modified-site
        ( B ) LOCATION: 32
        ( D ) OTHER INFORMATION: /note="The methionine at position
                32 is methionine amide."

( x ) PUBLICATION INFORMATION:
        ( A ) AUTHORS: Spindel, Eliot R.
                Krane, Ian M.
        ( B ) TITLE: Molecular Biology of Bombesin-like Peptides
        ( C ) JOURNAL: Ann. N. Y. Acad. Sci.
        ( D ) VOLUME: 547
        ( F ) PAGES: 10-20
        ( G ) DATE: 1988
        ( K ) RELEVANT RESIDUES IN SEQ ID NO:2: FROM 1 TO 32

( x i ) SEQUENCE DESCRIPTION: SEQ ID NO:16:

```
Ala Pro Leu Ser Trp Asp Leu Pro Glu Pro Arg Ser Arg Ala Ser Lys
1               5                   10                  15

Ile Arg Val His Ser Arg Gly Asn Leu Trp Ala Thr Gly His Phe Met
                20                  25                  30
```